(12) United States Patent
Berrido et al.

(10) Patent No.: US 7,548,684 B2
(45) Date of Patent: Jun. 16, 2009

(54) AIR TREATMENT APPARATUS AND REFILL PACK

(75) Inventors: Colin Berrido, Bagshot (GB);
Hans-Jurgen Huppert, Leipzig (DE)

(73) Assignee: Bell Flavours & Fragrances Limitd, Cambridge, Cambridgeshire (GB)

( * ) Notice: Subject to any disclaimer, the term of this patent is extended or adjusted under 35 U.S.C. 154(b) by 0 days.

(21) Appl. No.: 11/204,735

(22) Filed: Aug. 16, 2005

(65) Prior Publication Data

US 2006/0039685 A1   Feb. 23, 2006

(30) Foreign Application Priority Data

Aug. 19, 2004   (GB)   ................. 0418543.5

(51) Int. Cl.
*F24F 6/00*   (2006.01)
*F24F 6/08*   (2006.01)

(52) U.S. Cl. ........................ 392/390; 392/394
(58) Field of Classification Search ......... 392/356–394; 422/120–126; 239/34, 44, 135, 136
See application file for complete search history.

(56) References Cited

U.S. PATENT DOCUMENTS

| | | | | |
|---|---|---|---|---|
| 3,378,333 | A | * | 4/1968 | Brite .................. 422/236 |
| 3,806,323 | A | * | 4/1974 | Thompson .............. 422/122 |
| 3,986,838 | A | * | 10/1976 | Reichert ............... 422/126 |
| 4,734,560 | A | | 3/1988 | Bowen |
| 4,915,301 | A | | 4/1990 | Munteanu |
| 5,091,111 | A | | 2/1992 | Neumiller |
| 5,145,604 | A | | 9/1992 | Neumiller |
| 5,185,155 | A | | 2/1993 | Behan et al. |
| 5,246,603 | A | | 9/1993 | Tsaur et al. |
| 5,249,676 | A | | 10/1993 | Ashcraft et al. |
| 5,500,223 | A | | 3/1996 | Behan et al. |
| 5,647,052 | A | | 7/1997 | Patel et al. |
| 5,993,854 | A | | 11/1999 | Needleman et al. |
| 6,224,641 | B1 | | 5/2001 | Matzat et al. |
| 6,291,371 | B1 | | 9/2001 | Shefer et al. |
| 6,309,715 | B1 | | 10/2001 | Lindauer et al. |
| 6,370,311 | B1 | | 4/2002 | Basavanhally |
| 6,375,966 | B1 | | 4/2002 | Maleeny et al. |
| 6,413,476 | B1 | | 7/2002 | Barnhart |
| 6,541,565 | B2 | | 4/2003 | Hood et al. |
| 6,548,015 | B1 | | 4/2003 | Stubbs et al. |

(Continued)

FOREIGN PATENT DOCUMENTS

EP   0 328 370   8/1989

(Continued)

OTHER PUBLICATIONS

Computer-Generated English Translation of Specification, Claims and English Abstract of JP 2001-299893 dated Oct. 30, 2001.

(Continued)

*Primary Examiner*—Sang Y Paik
(74) *Attorney, Agent, or Firm*—Ladas and Parry LLP

(57) ABSTRACT

Air treatment apparatus comprises an electric heating element (5) and a refill pack containing wax or paraffin granules (2) incorporating a fragrance or other active substance eg. insect repellent. In another embodiment heat is supplied by a exothermic reaction mixture.

24 Claims, 11 Drawing Sheets

U.S. PATENT DOCUMENTS

| | | | |
|---|---|---|---|
| 6,703,011 B2 | 3/2004 | Shefer et al. | |
| 2001/0012495 A1 | 8/2001 | Furner et al. | |
| 2004/0000660 A1 | 1/2004 | Li | |

FOREIGN PATENT DOCUMENTS

| | | |
|---|---|---|
| EP | 1 065 252 | 1/2001 |
| FR | 2 565 109 | 12/1985 |
| GB | 2 192 337 | 1/1988 |
| GB | 2 199 246 | 7/1988 |
| GB | 2 327 349 | 1/1999 |
| JP | 2001-299893 | 10/2001 |
| RU | 1775119 | 11/1992 |
| WO | 97/09072 | 3/1997 |
| WO | 99/48469 | 9/1999 |
| WO | 02/05620 | 1/2002 |
| WO | 02/068005 | 9/2002 |
| WO | 2004/035721 | 4/2004 |

OTHER PUBLICATIONS

WPI / Derwent Abstract of FR 2 565 109 dated Dec. 6, 1985.
English Translation of Specification and WPI / Derwent Abstract of SU 1775119 dated Nov. 15, 1992.
espacenet.com English Abstract of Jan. 10, 2006 of JP 2001299893 of Oct. 30, 2001.
Derwent English Abstract of Nov. 7, 2005 of SU 19904822949 of Jul. 5, 1990.

* cited by examiner

AIR TREATMENT APPARATUS AND REFILL PACK

The present invention relates to a thermal air treatment apparatus and to a refill pack for such apparatus.

The term air treatment apparatus encompasses not only air freshener devices (which typically evaporate a scented oil from a wick which dips into a container of the oil, the oil being heated by e.g. an electric heater or a candle flame) but also similar apparatus in which the heated liquid contains a dissolved insect repellent or other active substance rather than a fragrance.

The above known devices thus contain spillable active substances and these can be hazardous in the home, especially because they are capable of being ingested by children. Furthermore, spilled liquid can damage sensitive surfaces such as carpets, textiles or furniture and even if a seal is provided, this is not always effective and in any case increases the manufacturing complexity.

In use, the wicks of heated liquid electric fragrance products can clog with unevaporated or decomposed fragrance components causing a loss of effectiveness. These fragrance components are typically volatile and sensitive to oxidation or hydrolysis and hence the conventional devices exhibit poor storage properties and a short shelf-life.

Products have been developed which dispense with a wick and with a heated liquid e.g. by incorporating the fragrance product in a polymer film but the manufacturer of such polymer films is complicated and expensive and furthermore such films can contain only a limited amount of fragrance or other active substance.

An object of the present invention is to overcome or alleviate at least some of the problems in the prior art.

In one aspect the invention provides air treatment apparatus for volatilising a fragrance or active substance, the apparatus comprising a receptacle containing particulate wax or paraffin or a heat transfer liquid having said fragrance or other active substance dispersed therein and controlled heating means which in use is arranged to heat said particulate wax or paraffin or heat transfer liquid to release said fragrance or other active substance into the atmosphere.

Figure 1:
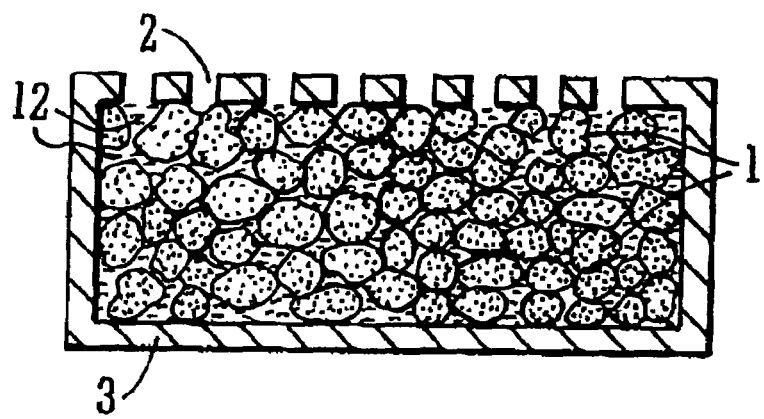
FIG. 1 is a schematic cross-section of a refill pack in accordance with the second aspect of the invention for use in an electrical thermal air treatment apparatus.

Apparatus according to the present invention does not require a wick and can dispense a fragrance or other active substance for a substantial period, since it is possible to incorporate a very substantial concentration of many fragrances and other active substances in solid wax or paraffin.

Preferably the controlled heating means is an electric heating element but in other embodiments the heating control may be provided by the addition of water or other temperature-limiting substance to the receptacle. In such embodiments the particulate wax or paraffin could be heated by a naked flame e.g. a candle or spirit lamp.

The term "wax" is to be understood in its broad sense i.e. not limited to substances containing esters or fatty acids but also encompassing long chain fatty alcohols or mixtures of fatty alcohols and fatty acids which are solid at ambient temperature.

In particular it is envisaged that the particulate material useful in air treatment apparatus of the present invention may comprise a waxy surfactant composition incorporating liquid fragrance, as disclosed in published International Application WO 2004/035721 (Bell Flavours & Fragrances Duft und GmbH) which is incorporated herein by reference and discloses the incorporation of up to 40 percent by weight of a liquid fragrance mixture in 60 percent by weight of a liquified C22 fatty alcohol which has been heated to a temperature a few degrees above the solidification point of 70° C.

The above application also discloses the dissolution of typically 40% and up to 60% by weight of a liquid fragrance mixture in a liquified mixture of 30 percent by weight C22 fatty alcohol and 30 percent by weight of stearin. The above application also discloses the incorporation of 40 percent by weight of fragrance in a liquified mixture of 30 percent by weight C22 fatty alcohol and 30 percent by weight polyethylene glycol.

Each of the above compositions is usable in the apparatus and refill pack of the present invention.

It is noted that the above International application discloses the use of such products in solid soaps, detergents, dishwashing agent and similar household chemicals as well as in cosmetic products. However use in air treatment apparatus is not disclosed or suggested.

Reference is also made to U.S. Pat. No. 6,224,641 which is incorporated herein by reference and discloses a process for producing a paraffin-based object, especially a candle, in which the perfume is dissolved in a solvent containing an organic ester, and this solution is in turn added to or dissolved in a paraffin which is subsequently solidified. The fragrance-loaded paraffin disclosed therein can be reduced to particulate form and utilised in the apparatus of the present invention.

Other active substances besides fragrances (e.g. insect repellents) can be dissolved in the waxes or paraffin-based products of WO 2004/035721A or U.S. Pat. No. 6,224,641.

Waxes and paraffins are chemically inert towards fragrances and other active substances utilised in air treatment apparatus and, besides avoiding the problems associated with spillage and spoilage of liquid products, have the following further advantages:

a) the fragrance or other active substance is retained within the wax or paraffin at ambient temperature and hence no seal is required;

b) manufacture is simpler and safer because the use of volatile organic liquid is avoided;

c) on initial heating, the fragrance or active substance is released gradually by diffusion from the particulate wax or paraffin, which can optionally be heated to its melting point to release substantially all the fragrance or other active substance, and d) in preferred embodiments, two or more fragrances can be incorporated in the wax or paraffin and released at different temperatures, and/or a mixture of waxes or paraffins having different melting points can be used, enabling a desired release profile of two or more fragrances to be achieved.

Heat transfer liquids that can be used to disperse the fragrance or other active substance(s) according to some embodiments of the invention include water, glycols, alcohols with boiling points above 100° C., mineral oils and silicone oils.

A variety of heating techniques may be used including electrical heating using, for example using a heating coil or element, direct heating by local combustion of, indirect heating using a heat transfer device or by local heat generation using an exothermic reaction. The use of indirect heating permits the use of replaceable heating units, for example a pack or heating stick containing the heat generating chemicals that may be inserted into and withdrawn from or placed adjacent to and distanced from the particulate wax or paraffin loaded with fragrance or other active substance(s) so as to control the time when said fragrance or active substance(s) are released.

In one embodiment, the control heating means is an electric heating element, which preferably has means, e.g. a positive temperature coefficient of resistance or a control circuit for self-limiting the heating of the particulate wax or paraffin.

In another embodiment the control heating means may comprise an exothermic reaction mixture, e.g. comprising calcium oxide (which generates heat on contact with water) or filings of an iron-magnesium alloy which generates heat by self-corrosion when added to an electrolyte substance such as sodium chloride solution. The use of dry heat packs based on heat generation by oxidation of iron filings by air may also be possible.

When heat is generated by the contact of calcium oxide with water, the particle size of the calcium oxide should be quite fine, to maximise the surface area that can contact the water, for example particles with an average diameter in the range 0.1 to 5 mm. We have, however found that in some cases clumping of the particles may occur at particle sizes of less than 0.5 mm. Typically a molar excess of water will be used.

When heat is generated by exothermic reaction, we have found that use of water-activatable heat-generating chemicals is most convenient since the use of water to activate the chemical(s) provides a number of different ways of controlling the heat generation. Such techniques can include simply allowing water to contact the chemical(s) direct from a source or if a more gradual contacting is desired to pass the water through a porous layer prior to contacting the chemical(s) Such layers. For example in the form of a sintered filter such as those used as HEPA filters. Such filters may be made of for example sintered ceramic or sintered polymer. Other means for controlling generation of heat for release of fragrance or active substance(s) include devices in which the water activatable chemicals may be lowered into or lifted from water and devices where heating is indirect so that the water-activatable heat source may be moved into or out of proximity with the fragrance- or active substance-containing granules or heat transfer liquid.

Preferably the reaction mixture is arranged in use to generate steam which volatilises the fragrance or other active substance. In this manner the fragrance or active substance is subjected to a steam distillation effect.

In another aspect the invention provides a refill pack for a thermal air treatment apparatus, the refill pack comprising a receptacle containing particulate wax or paraffin having a fragrance or other active air treatment substance absorbed therein, said receptacle having a perforated or permeable wall for releasing said fragrance or other active air treatment substance into the atmosphere and said receptacle being sufficiently heat resistant to enable it to be heated in such an apparatus to a temperature sufficient to release the fragrance or other active substance into the atmosphere.

Such a refill pack will have a very long storage life, owing to the inertness of solid waxes and paraffins towards fragrances and other active substances and furthermore the problems of spillage are completely avoided.

Preferably the receptacle is made of metal such as aluminium, but in some embodiments intended for relatively gentle heating, a heat resistant plastics material may be used instead.

In one embodiment the receptacle contains an exothermic reaction mixture (e.g. either of the reaction mixtures noted above) and this reaction mixture is preferably in contact with the particulate wax or paraffins.

Optionally, the refill incorporates water which in use generates steam which fullatilises the fragrance or other active substance.

Preferably the refill incorporates a frangible barrier portion which can be broken to bring the water into contact with the reaction mixture.

Further preferred features of the invention are defined in the dependent claims.

Preferred embodiments of the invention are described below by way of example only with reference to FIGS. 1 to 7 of the accompanying drawings, wherein:

FIG. 1 depicts one example of a refill in accordance with the invention. It consists of a heat resistant/conducting container 3 with vents 2 to allow granules 1 of wax or paraffin loaded with fragrance or other active substance(s) to communicate with the intended environment. The granules 1 can be optionally surrounded by a gel matrix 12 to enhance handling or performance.

Figure 2:
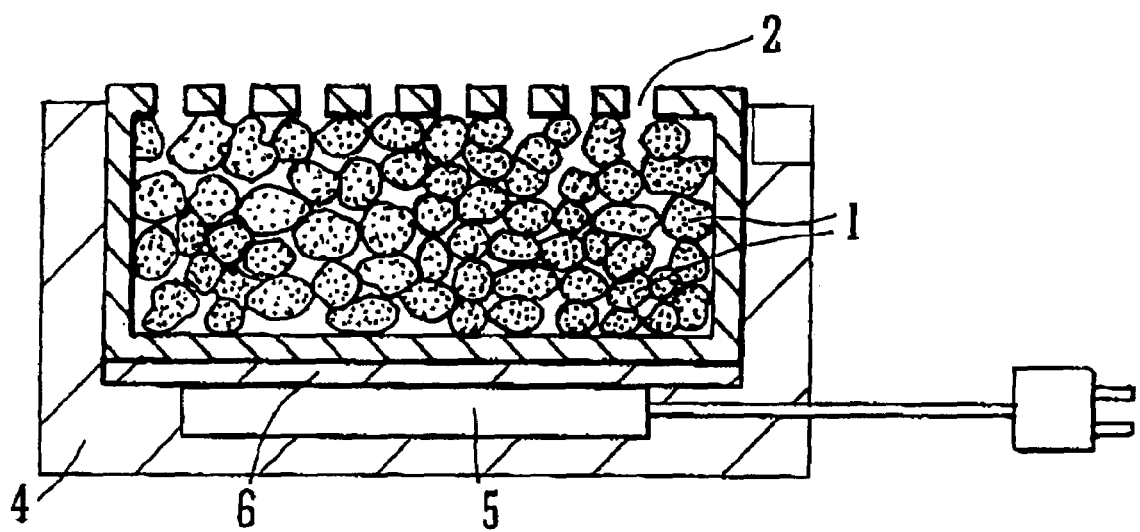
FIG. 2 is a schematic cross-section showing an air treatment apparatus in accordance with the first aspect of the invention and utilising a refill as shown in FIG. 1.

FIG. 2 shows the embodiment of FIG. 1 placed in a heating assembly consisting of a housing 4, a ptc heating element 5, and a heat transfer plate 6 to moderate heat fluctuations, distribute heat evenly and moderate temperature.

Figure 3:
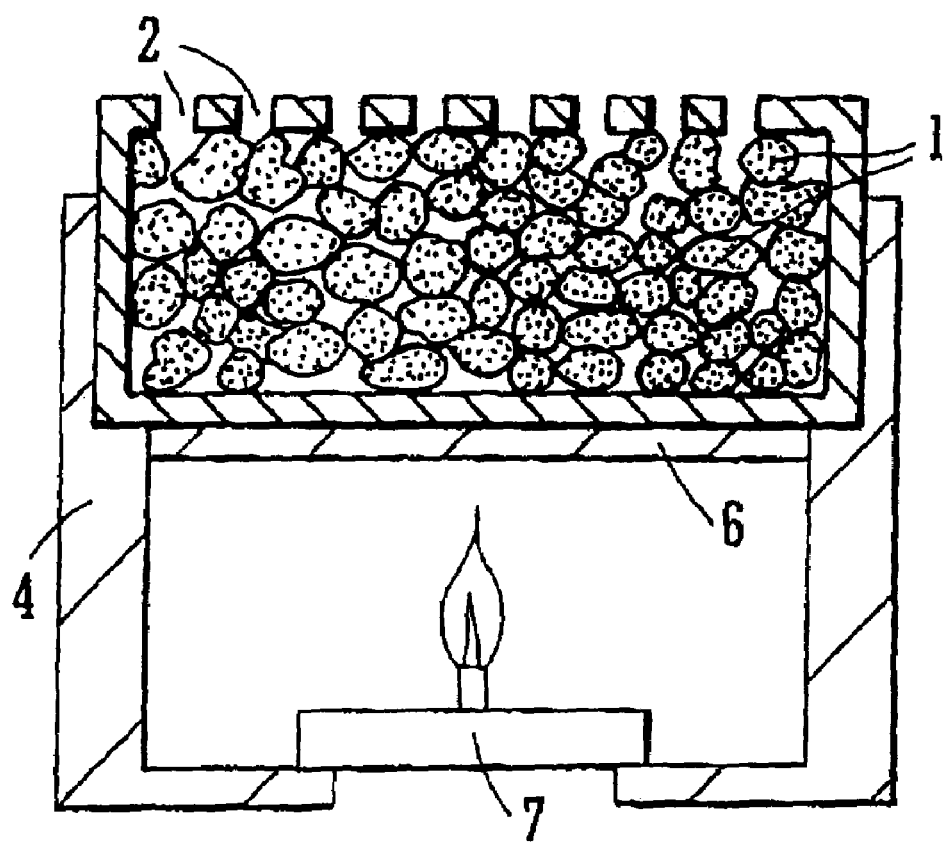
FIG. 3 is a schematic cross-section of a further embodiment of the apparatus of the first aspect of the invention, again utilising a refill as shown in FIG. 1.

FIG. 3 shows another embodiment of the invention whereby the refill of FIG. 1 is placed in a housing 4 designed to hold a T-lite candle 7 that is used as a source of heat. A heat transfer plate 6 is added to moderate heat flow as described in the description for FIG. 2.

Figure 4:
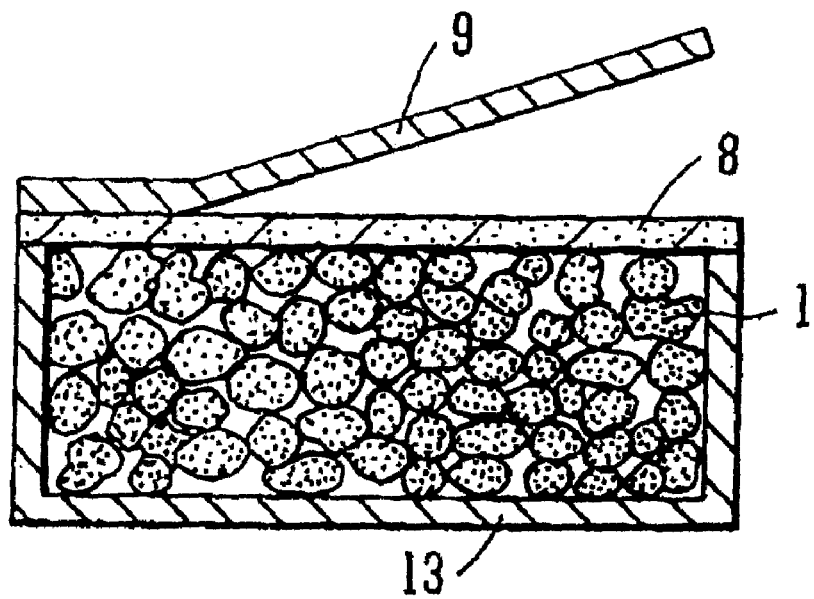
FIG. 4 is a schematic cross-section showing a variant of the refill pack of FIG. 1.

FIG. 4 illustrates an example of a refill that uses a permeable membrane 8 instead of vents as depicted in FIGS. 1 and 2, as a means to allow transport of the active(s) from the granules of fragrance—loaded wax or paraffin 1 to its intended environment A peelable lidding 9 is used to seal the refill prior to use. In this example, the housing is made of thermoformable heat stable plastic 13 to allow the refill to be used in a heater or to withstand chemically induced heat The housing could also be electrostatically coated or laminated with a heat conductive coating (e.g. metalized film).

Figure 5:
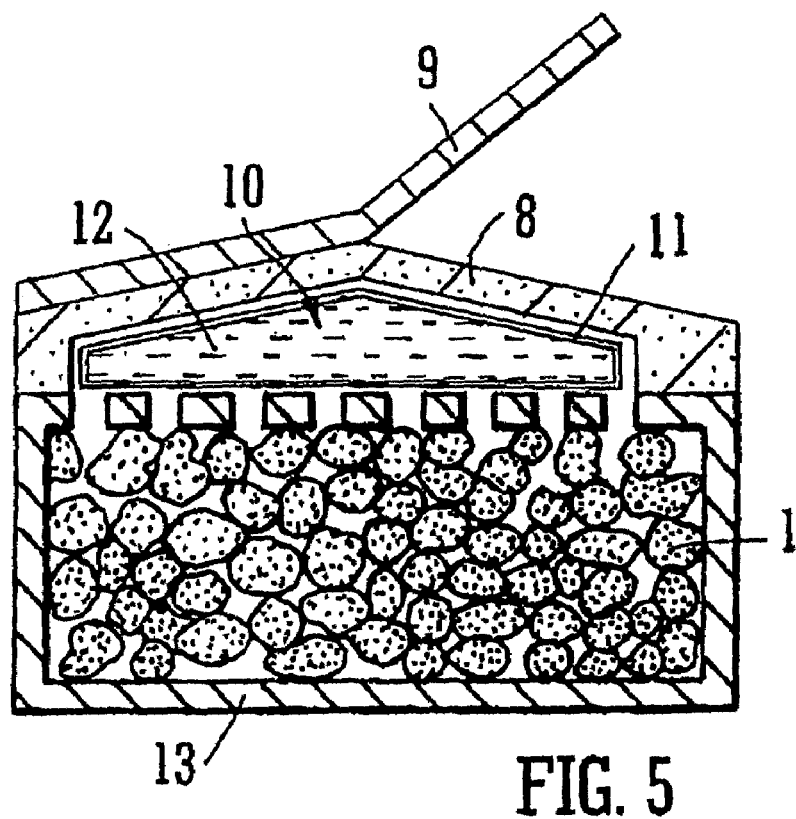
FIG. 5 is a schematic cross-section showing a further variant of the refill of FIG. 1 incorporating a burstible sachet of water.

FIG. 5 depicts yet another embodiment of this invention that includes a means to additional components to the granules of fragrance loaded wax or paraffin just prior to use. Water 12 used in this example is used to enhance the evaporation of the active(s) by providing an azeotropic or steam distillation effect and offer thermal limitation (it is to be noted that other material and or mixtures besides water can be used to augment, activate or regulate the active). However in its simplest form the activator can be added manually after opening of the refill, or, pre-added prior to sealing of the refill.

The device of FIG. 5 consists of a vented housing made with thermoformable heat stable plastic 13 containing granules of fragrance loaded wax or paraffin that is covered with a burstable seal 11 incorporated into a burstable sachet 10. The burstable sachet is covered with a permeable membrane 8 to allow transport of the active(s) to its intended environment A peelable lidding 9 is included to seal the refill prior to use.

Figure 6:
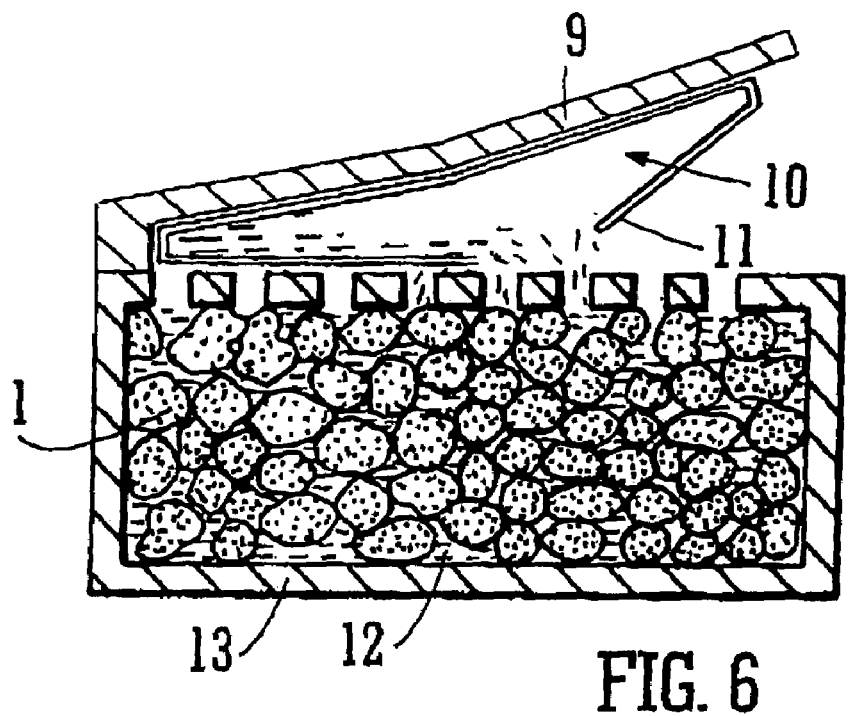
FIG. 6 is a schematic cross-section showing a further variant of the refill of FIG. 1.

FIG. 6 shows a modification of the embodiment of FIG. 5 whereby the burstable sachet 10 is attached to the peelable lidding 9. (In this drawing, the burstable seal has already been activated.) Vents are used instead of a semi-permeable membrane as depicted in FIG. 5.

Figure 7:
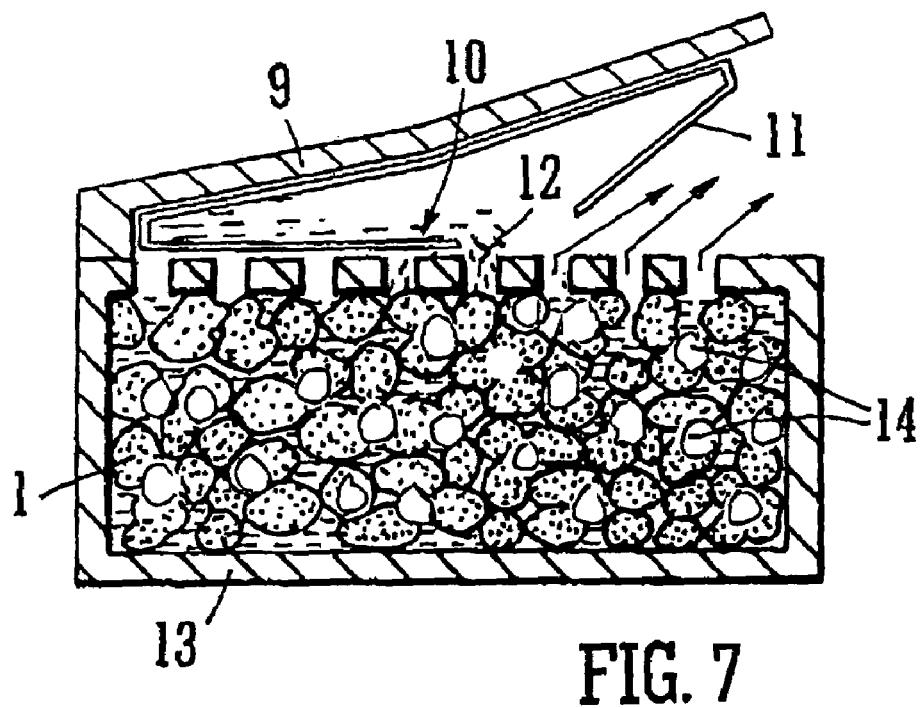
FIG. 7 is a schematic cross-section of a further variant of the refill of FIG. 1.

FIG. 7 shows yet another embodiment that requires no external source of heat to augment the performance of the active(s). In this embodiment, an exothermic reaction is used to provide heat from within the product. Calcium oxide is used in this example as the heat-generating chemical. However, it is understood that other chemistries can be used such as iron and magnesium alloy fillings mixed with salt and water to catalyze an electrolytic reactive which generates heat. This embodiment is similar in construction to that of FIG. 6; however, a reacting chemical (in this case CaO) is mixed with the granule 1. In operation, the product is squeezed to burst the burstable sachet 10 to release water 12 into the mixture of granules 1 and chemical 14 (CaO) prior to opening the product via peelable lid 9. The resulting exothermic reaction caused by the admixture of water with the CaO 14 provides heat to augment the performance of the active(s) contained in the granules 1. This allows the product to be easily portable since a driven electrically power source is not required.

Figure 8:
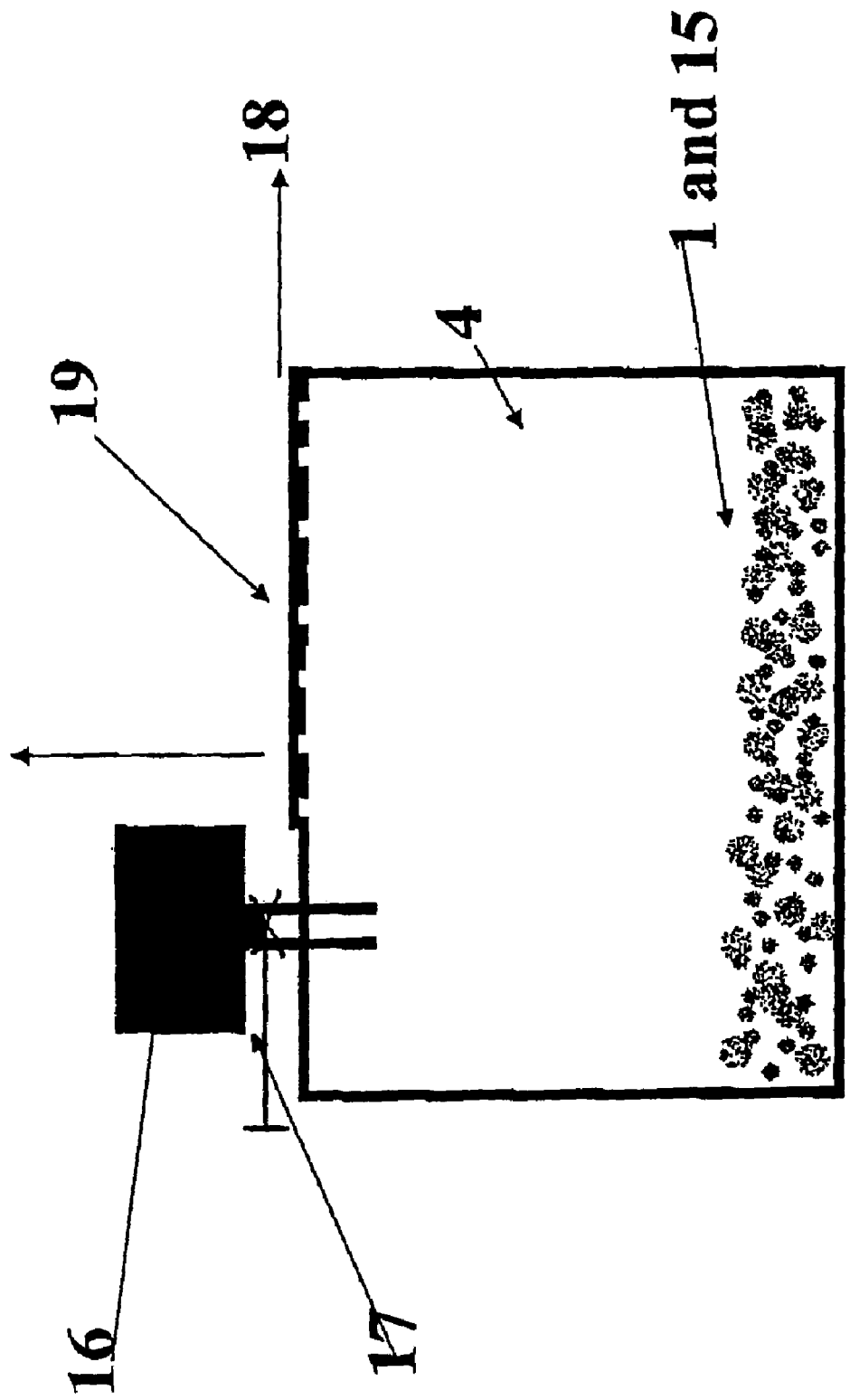
FIG. 8 is a schematic cross-section of an embodiment of the invention where heat is generated by addition of water through a simple control valve.

FIG. 8 shows a container 14, which may be thermally insulated, containing a mixture of granules 1 of wax or paraffin loaded with fragrance or other active substance(s) and powdered chemical(s) 15 capable of generating heat when contacted with water. The top of the container is fitted with a water reservoir, 16, which is optionally pre-sealed, and can allow water to enter the container through a valve 16. This valve is conveniently manually operated but in particular circumstances could be controlled mechanically, for example by a timer or in response to signal from a sensing device of some type. The top surface of the container is fitted with vents through which the fragrance or other active substance may be released. In the particular embodiment shown, a sealing foil 19 is provided that can be peeled off . Other forms of closure or even no closure may, however, be used if desired.

Figure 9:
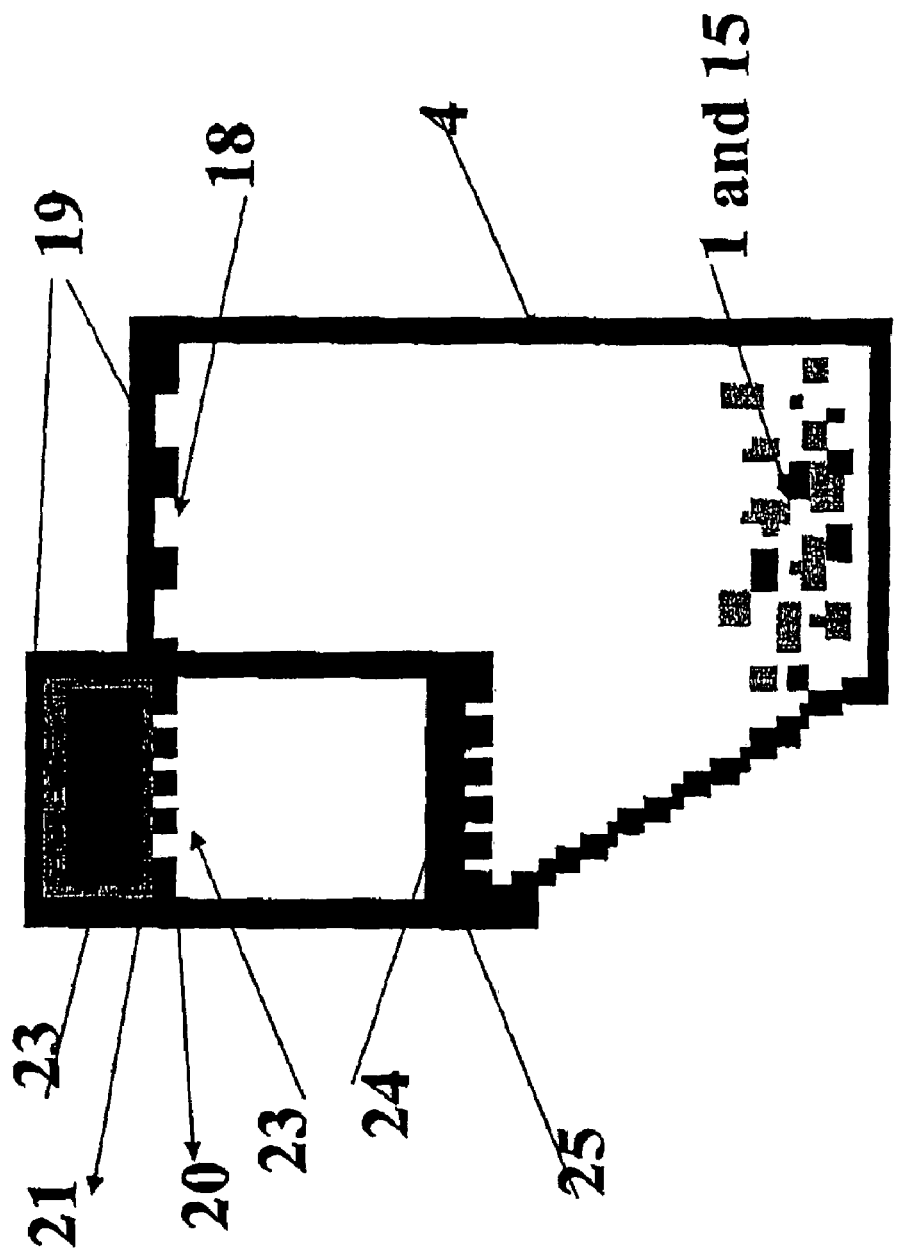
FIG. 9 is a schematic cross-section of an embodiment of the invention where heat is generated by addition of water through a sintered control valve.

FIG. 9 shows an embodiment similar to that shown in FIG. 8 except that in this case the water supply is provided by a unit 20 comprising a upper and lower compartments 21, 22 having apertures on their lower sides, the upper compartment being adapted to contain a water sachet and the lower compartment having a sintered control valve formed of a porous material through which water released from the sachet may pass before entering the main container and contacting the water-activatable heat-generating chemical(s). The rate at which water will pass into the main chamber will be controlled by the degree of porosity of the sintered control valve. p The sachet may be burst manually to release water. Alternatively provision of an air-tight seal over the vents of the main compartment permits the control of the release of water from the water supply unit by maintaining sufficient pressure in the main container to prevent water from entering it until the seal is removed. When this occurs, water can then start to flow from the sachet through the control valve and so activate the heat-generating chemical(s).

Figure 10:
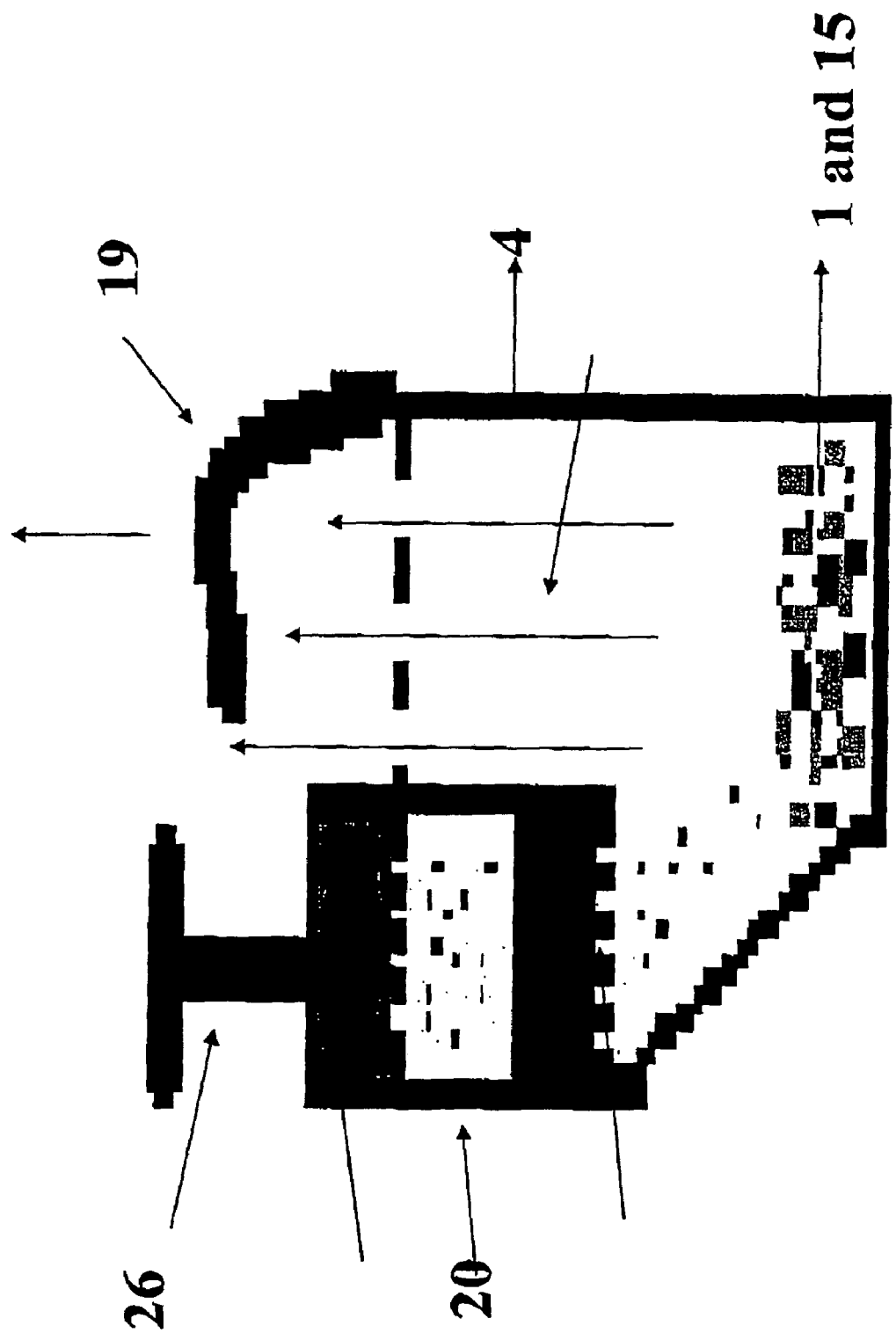
FIG. 10 is a schematic cross-section of an embodiment of the invention where heat is generated by addition of water by bursting a water-containing sachet.

FIG. 10 shows a modification of the embodiment shown in FIG. 9 in which a mechanism 23 including a sharp surface is provided for puncturing the water sachet.

Figure 11:
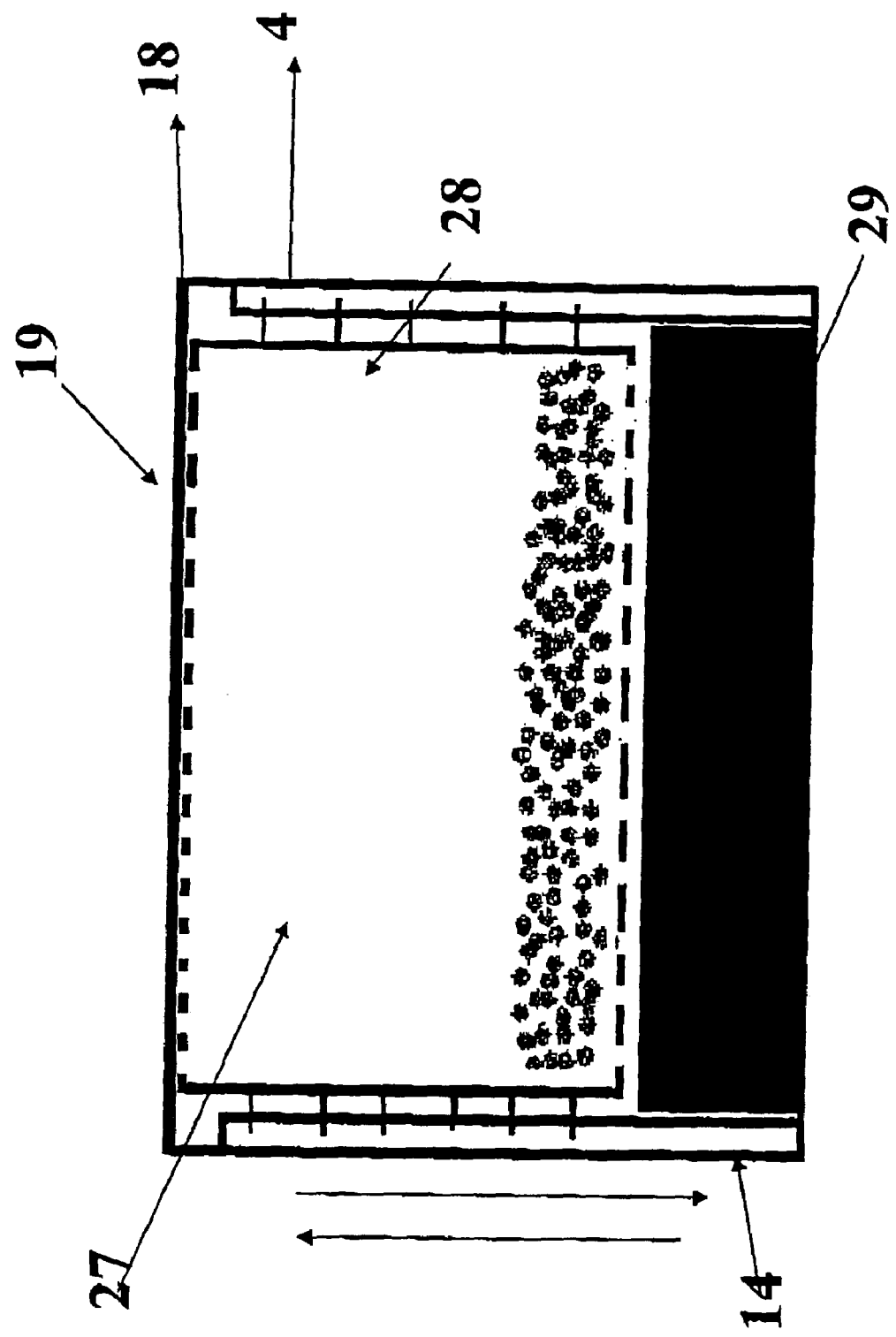
FIG. 11 is a schematic cross-section of an embodiment of the invention where heat is generated by addition of water using a mechanism to permit control of reactive chemicals with water when the chemicals are out of contact with water.
Figure 12:
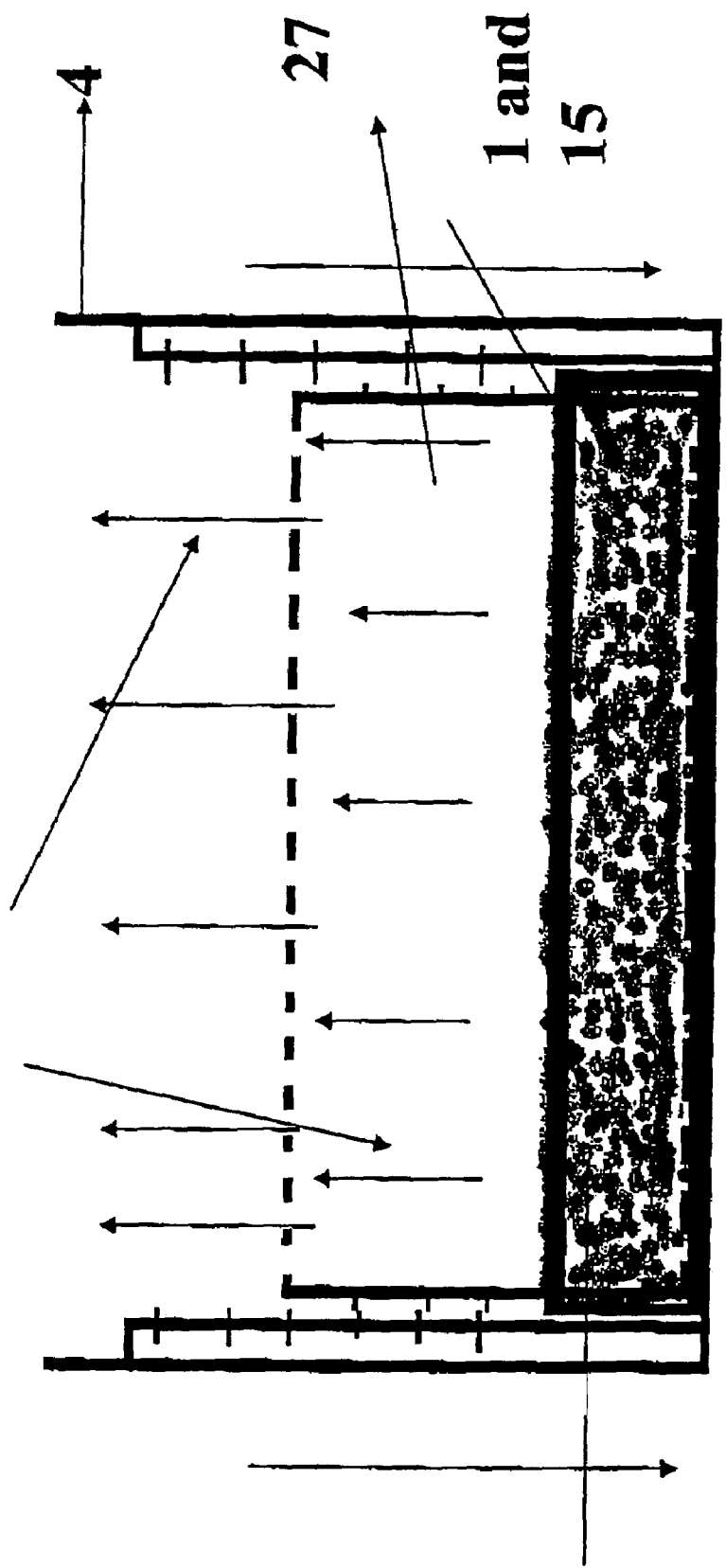
FIG. 12 is a schematic cross-section of the embodiment of FIG. 11 when the chemicals are in contact with water.

FIGS. 11 and 12 show and embodiment of the invention in which a basket or cage 24 containing water-activatable heat-generating chemical(s) and granules of wax or paraffin loaded with fragrance or other active substance(s)can be raised from or lowered into water. The raising and lowering can be effected by use of a ratchet mechanism 25. Water can conveniently be provided by a burstable sachet 26, although other methods of placing water in the base of the container may be used. If a cage is used to contain the chemicals, this may conveniently have vents at the top that are covered with a peelable seal prior to use. If an open toped basket is used, the top of the container may be provided with vents over which a peelable seal may be placed.

Figure 13:
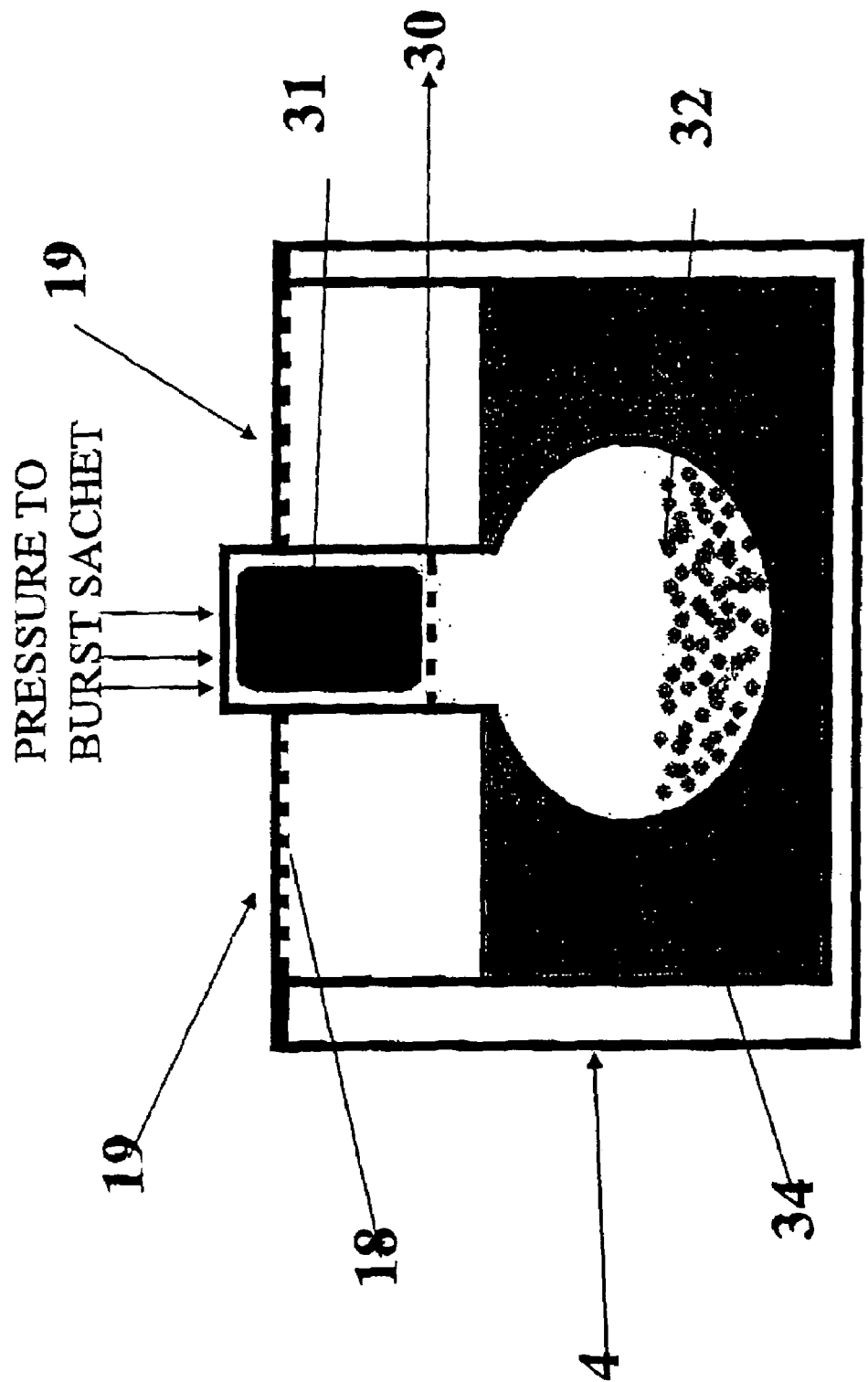
FIG. 13 is a schematic cross-section of an embodiment of the invention where heat is generated by addition of water to chemicals that are isolated from the particulate wax or paraffin which are heated by heat transfer.
Figure 14:
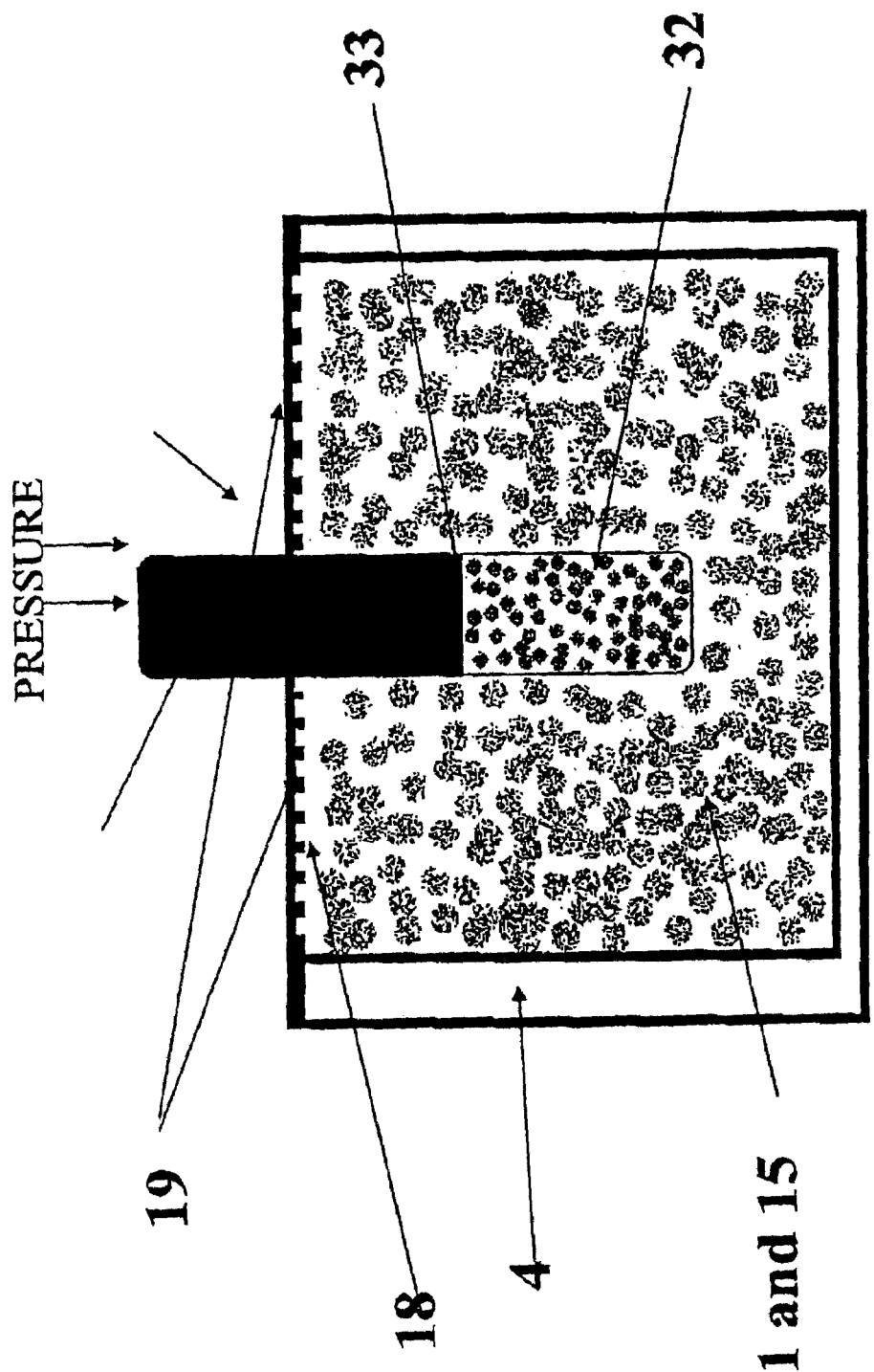
FIG. 14 is a schematic cross-section of an embodiment of the invention using a replaceable heating stick.

FIGS. 13 and 14 show embodiments of the invention wherein heat transfer to fragrance or other active substance(s) is effected indirectly by a heat transfer mechanism. In both embodiments an optionally removable heating unit 27 in which a water-containing sachet 28 is mounted above heat generating chemicals 29 so that when the sachet is ruptured, water will drop from the sachet onto the chemicals. Such an assembly is desirably self-contained and removable, for example it can form a "heat stick". The assembly typically is designed so that when pressure is applied to the water containing sachet a burstable seal 30 or lower part of the sachet bursts in such manner as to bring the water into contact with the heat-generating chemicals. Such heating units may be inserted into a container 14 containing granules of wax or paraffin loaded with fragrance or other active substance(s) as shown in FIG. 14. Alternatively, the fragrance or other active substance(s) may be dissolved or dispersed in a heat transfer liquid 31 contained in the container as shown in FIG. 13.

The invention claimed is:

1. Air treatment apparatus for volatilising a fragrance or active substance, the apparatus comprising a receptacle containing water in contact with particulate wax or paraffin, said particulate wax or paraffin having said fragrance or other active substance dispersed within particles of the wax or paraffin, and controlled heating means for heating said particulate wax or paraffin to release said fragrance or other active substance from within the wax or paraffin and into the atmosphere.

2. Apparatus according to claim 1, wherein said controlled heating means is an electric heating element.

3. Apparatus according to claim 2, wherein said electric heating element has means for self-limiting the heating of said particulate wax or paraffin.

4. Apparatus according to claim 1, wherein said controlled heating means comprises an exothermic reaction composition.

5. Apparatus according to claim 4, further comprising a closed container of water and means for bringing the water from said container into contact with said reaction composition.

6. Apparatus according to claim 5, wherein said container of water has a frangible portion for releasing the water into said reaction composition.

7. Apparatus according to claim 4, wherein said exothermic reaction composition is activated by contact with water.

8. Apparatus according to claim 4, wherein said exothermic reaction mixture is in contact with said particulate wax or paraffin and is arranged in use to volatilise said fragrance or other active substance therefrom.

9. Apparatus according to claim 4, wherein the exothermic reaction composition comprises calcium oxide.

10. Apparatus according to claim 4, wherein said exothermic reaction composition is arranged in use to generate steam which volatilises said fragrance or other active substance.

11. Apparatus according to claim 1, wherein said controlled heating means is arranged to melt said particulate wax or paraffin.

12. Apparatus according to claim 1, wherein said particulate wax or paraffin is in the form of granules, the granules being sufficiently loosely packed to allow release of fragrance or other active substance from the interstices of the packed granules.

13. Apparatus according to claim 11, wherein the mean diameter of said granules is in the range 2 to 8 mm.

14. Apparatus according to claim 1, wherein said fragrance and/or other active substance comprises two or more components of different volatility which in use are preferentially released at different stages as the particulate wax or paraffin is heated.

15. Apparatus according to claim 1, wherein said wax or paraffin comprises two or more components of different melting point whereby the wax or paraffin is arranged in use to melt progressively on heating.

16. Apparatus according to claim 1, wherein said particulate wax or paraffin comprises a long-chain fatty alcohol or a mixture of long-chain fatty alcohols and fatty acids and optionally contains a fatty alcohol ethoxylate and/or polyethylene glycol.

17. Apparatus as claimed in claim 4, wherein water-activatable heat generating chemical(s) are mixed with granules of wax or paraffin having said fragrance or other active substance dispersed therein.

18. Apparatus as claimed in claim 1, wherein said heating is effected by indirect means.

19. Apparatus as claimed in claim 1, wherein said fragrance or other active substance or substances is dispersed in heat transfer liquid selected from water, glycols, alcohols with boiling points above 100° C., mineral oils, silicone oils and mixtures thereof.

20. Apparatus as claimed in claim 18, wherein the heat-generating composition is contained in a replaceable unit.

21. Apparatus according to claim 1, wherein water is fed into contact with said heat-generating composition through a sintered filter.

22. Apparatus according to claim 1, wherein means are provided for raising or lowering the heat generating composition into and from water.

23. An air treatment apparatus for volatilizing a fragrance or other active substance comprising:

(i) a particulate wax or paraffin having at least one fragrance or other active substance dispersed within particles of said wax or paraffin such that the particulate wax or paraffin retains the fragrance or other active substance within particles of the wax or paraffin at an ambient temperature below a melting point of the wax or paraffin and releases substantially all of the fragrance or other active substance when the particles are heated to the melting point of the wax or paraffin;

(ii) a receptacle for containing the particulate wax or paraffin having the fragrance or other active substance dispersed therein; and (iii) means for controlled heating of the particulate wax or paraffin within the receptacle by reaction of a chemical substance and water that generates steam which volatilizes the fragrance or other active substance such that the fragrance or other active substance is gradually released by diffusion from the particulate wax or paraffin.

24. The apparatus according to claim 23, wherein the at least one fragrance or other active substance is dispersed in the paraffin by a process comprising (a) loading the paraffin with the at least one fragrance or other active substance before the paraffin is reduced to particulate form and (b) then reducing the paraffin to particulate form.

* * * * *

UNITED STATES PATENT AND TRADEMARK OFFICE
CERTIFICATE OF CORRECTION

PATENT NO.       : 7,548,684 B2                                         Page 1 of 1
APPLICATION NO.  : 11/204735
DATED            : June 16, 2009
INVENTOR(S)      : Colin Berrido et al.

It is certified that error appears in the above-identified patent and that said Letters Patent is hereby corrected as shown below:

On the Title Page Item (73), Assignee's name, "Limitd" should read -- Limited --

Signed and Sealed this

First Day of September, 2009

David J. Kappos
*Director of the United States Patent and Trademark Office*